(12) United States Patent
Fantus

(10) Patent No.: US 6,258,848 B1
(45) Date of Patent: Jul. 10, 2001

(54) METHODS AND COMPOSITIONS FOR INCREASING INSULIN SENSITIVITY

(75) Inventor: I. George Fantus, Toronto (CA)

(73) Assignee: Mount Sinai Hospital, Toronto (CA)

( * ) Notice: Subject to any disclaimer, the term of this patent is extended or adjusted under 35 U.S.C. 154(b) by 0 days.

(21) Appl. No.: 09/364,637

(22) Filed: Jul. 30, 1999

Related U.S. Application Data (60) Provisional application No. 60/133,261, filed on May 10, 1999, and provisional application No. 60/094,835, filed on Jul. 31, 1998.

(51) Int. Cl.$^7$ .................................................. A61K 31/195

(52) U.S. Cl. .......................................................... 514/562

(58) Field of Search ............................ 514/562, 2, 474, 514/458, 725; 424/195.1, 639, 641, 646, 655

(56) References Cited

FOREIGN PATENT DOCUMENTS

| | | |
|---|---|---|
| 297 07 005 U | 6/1997 | (DE) . |
| 339 508 | 11/1989 | (EP) . |
| 0 486 921 | 5/1992 | (EP) . |
| WO 85/02340 | 6/1985 | (WO) . |
| WO 98 30228 | 7/1998 | (WO) . |

OTHER PUBLICATIONS

Mostafa, Y.H. et al "Modulatory effects of N–acetylcysteine and alpha–tocopherol on brain glutathione and lipid peroxides in experimental diabetic and endotoxin stressed rats." *Sandi Pharm. Journal* (1994), 2(2), 64–9, XP000870276. Abstract, p. 66, column 1, paragraph 2; p. 68, column 1, paragraph 3.

Ammon, H.P. et al. "Cysteine analogues potentiate glucose–induced insulin release in vitro." *Diabetes* (Dec. 1986), 35(12), 1390–6, XP000870090. Abstract.

Keegan, A. et al. "Metal chelator and free radical scavenger treatments prevent chronic aorta relaxation defects in diabetic rats." *Diabetologia* (1996), vol. 39, No. Suppl. 1, pp A240. Meeting Info.: 32$^{nd}$ Annual Meeting of the European Association for the Study of Diabetes, Vienna, Austria, Sep. 1–5, 1996, XP000870277. Abstract.

Alvira, D. Romero et al. "Diabetes. Cytotoxic damage caused by free radicals!. Libres." *Endocrinologia* (1991) 38/6 (190–197), XP000874000. The whole document.

Sagara, M. et al "Inhibition of development of peripheral neuropathy in streptozotocin–induced diabetic rats with N–acetylcysteine." *Diabetologia* (1996), 39(3), 263–9, XP–000870081. Abstract.

Van Dam, P. Sytze et al. "Oxidative stress and antioxidant treatment in diabetic neuropathy." *Neuroscience Research Communications* (1997), vol. 21, No. 1, pp. 41–48, XP000870060. Abstract.

Carmeron, N.E. et al. "Chronic N–acetyl–L–cysteine treatment prevents impaired endothelium–dependent relaxation and improves peripheral nerve blood flow and conduction in diabetic rats." *European Journal of Clinical Investigation* (1995), vol. 25, No. Suppl. 2, pp. A9., Meeting Info.: 29$^{th}$ Annual Meeting of the European Society for Clinical Investigation and the Medical Research Society of Great Britain, Cambridge, England, UK Apr. 2–5, XP000870051. Abstract.

Wentzel, Parri et al. "Antioxidants diminish developmental damage induced by high glucose and cyclooxygenase inhibitors in rat embryos in vitro." *Diabetes* (1998), 47(4), 677–684, XP000870086. Abstract.

PCT Search Report for the corresponding international application, Feb. 7, 2000(PCT/CA99/00488).

Cahill G.F. Jr. (1976), J. Clin. Endocrinol. Metab. 5: 397–415.

Bergman R.N. (1989), Diabetes. 38: 1512–1527.

Himsworth H. and Kerr R.B. (1942), Clin. Sci. 4: 120.

Kahn C.R. (1978), Metabolism. 27: 1893–1902.

Olefsky J.M. (1981), Diabetes. 30: 148–161.

Reaven G.M. (1988), Diabetes. 37: 1595–1607.

Kahn C.R. et al, in Pathogenesis of Non–Insulin Dependent Diabetes Mellitus. Grill V, Efendeic S. Eds. (1988) New York Raven p. 227–239.

DeFronzo R.A., et al., (1992), Diabetes Care 15:318–368.

Kolterman G et al (1981), J. Clin. Invest. 68: 957–969.

Porte D. Jr. (1991), Diabetes. 40:166–180.

Leahy J., et al (1992), Diabetes Care 15: 442–455.

Turner R et al (1992), Ann. of Med. 24(6):511–516.

Moller DE, Flier JS (1991), N. Engl. J. Med. 325:938–948.

Taylor S.I. et al (1991), J. Clin. Endocrinol. Metab. 73:1152–1163.

Kahn C.R., (1994), Diabetes 43: 1066–1084.

Krunszynaka Y.T. and Olefsky J.M. (1996), J. Invest. Med. 44: 413–428.

Rodbell, M. (1964) J. Biol. Chem. 238,375–380.

Rothman D.L. et al (1992), J. Clin. Invest. 89: 1069–1075.

Rothman D.E. et al (1995), Proc. Natl. Acad. Sci. USA. 92: 983–987.

Shulman, G.I. et al (1990), N. Engl. J. Med. 322: 233–228.

Ciaraldi T.P. et al (1982), Diabetes 32: 1016–1022.

Kashiwagi A. et al (1983), J. Clin. Invest. 72: 1246–1254.

Marshall S., Olefsky, J.M. (1980), J. Clin. Invest. 66: 763–772.

Olefsky, J.M., Biochem J. 172: 137–145, 1978.

Marshall S. et al (1991), FASEB J. 5:3031–3036.

(List continued on next page.)

Primary Examiner—Raymond Henley, III
(74) Attorney, Agent, or Firm—Merchant & Gould P.C.

(57) ABSTRACT

A method of increasing insulin sensitivity in a subject by administering an effective amount of N-acetyl cysteine, and methods for treating conditions requiring an increase in insulin sensitivity are described. Pharmaceutical compositions are contemplated for use in preventing or treating a condition requiring increasing insulin sensitivity or reducing insulin resistance comprising an effective amount of N-acetyl cysteine, and a pharmaceutically acceptable carrier, diluent, or excipient.

4 Claims, 6 Drawing Sheets

OTHER PUBLICATIONS

Garvey WT, et al (1987), J. Biol. chem. 262: 189–197.
Traxinger PR, Marshall S (1989), J. Biol. Chem. 264: 8156–8163.
Marshall, S., et al (1991), J. Biol. Chem 266:4706–4712.
McClain D.A., Crook E.D. (1996), Diabetes 45: 1003–1009.
Robinson, K.A. et al (1993), Diabetes 42: 1333–1346.
Baron A.D. et al (1995), J. Clin. Invest. 96: 2792–2801.
Rosetti L. et al (1995), J. Clin. Invest. 96: 132–140.
Beutler B. et al (1985), Nature 316: 552–554.
Hostamisligil G.S., Spiegelman B.M. (1994), Diabetes 43: 1271–1278.
Hostamisligil G.S., et al (1993), Science 259: 87–91.
Skolnik E.Y., Marcusohn J. (1996), Cytokine & Growth Factor Reviews 7: 161–173.
Hotamisligil G.S., et al (1995), J. Clin. Invest. 95: 2409–2415.
Stephens J.M. et al (1997), J. Biol. Chem. 272:971–976.
Douglas R.G. et al (1991), Am. J. Physiol. 261, 606–612.
C.H. Lang et al, Endocrinology 130, 43–52 (1992).
Hotamisligil G.S. et al (1994), J. Clin. Invest. 1543–1549.
Hotamisligil G.S. et al (1994), Proc. Natl. Acad. Sci. USA 91: 4854–4858.
Feinstein R. et al (1993), J. Biol. Chem. 268: 26055–26058.
Hotamisligil G.S. et al (1996), Science 271: 665–668.
Kanety H. et al (1995), J. Biol. Chem, 270: 23780–23784.
Wolff S.P., Dean R.T. (1987), Biochem J. 245: 243–250.
Kashiwagi A. et al (1994), Diabetologia 37: 264–269.
Wohaieb S.A., Godin D.V. (1987), Diabetes 36: 1014–1018.
Muller H.K. et al (1991), Diabetes 40: 1440–1448.
Berti L. et al (1994), J. Biol. Chem. 269: 3381–3386.
Takayama S. et al (1988), J. Biol. Chem. 263: 3440–3447.
Kunisaki M. et al (1994), Diabetes 43: 1372–1377.
Lo Y. Y. et al (1996), J. Biol. Chem. 271: 15703–15707.
Sulciner D.J. et al (1996), Mol. Cell Biol. 16: 7115–7121.
Lo Y.Y.C. et al (1995), J. Biol. Chem. 270: 11727–11730.
Meier B. et al (1989), Biochem J. 263: 539–545.

● Control
■ Glucosamine (2.5mM)
▲ High insulin(600ng/ml)/High Glucose(20mM)

METHODS AND COMPOSITIONS FOR INCREASING INSULIN SENSITIVITY

This application is a Utility Application claiming benefit under Title 35, United States Code §119(e) of Provisional Application Ser. No. 60/094,835, filed Jul. 31, 1998 and Provisional Application Ser. No. 60/133,261, filed May 10, 1999.

FIELD OF THE INVENTION

The invention relates to methods and compositions for increasing insulin sensitivity.

BACKGROUND OF THE INVENTION

Glucose homeostasis depends upon the balance between hepatic glucose production and glucose utilization by insulin-dependent tissues, such as fat, muscle and liver, and by insulin-independent tissues such as brain and kidney [Cahill G. F. Jr. (1976), J. Clin. Endocrinol. Metab. 5: 397–415; Bergman R. N. (1989), Diabetes. 38: 1512–1527].

This balance is controlled by pancreatic hormones, insulin from the β-cell of the pancreatic islet and glucagon from the α-cell. In normal individuals, an increased plasma glucose stimulates insulin secretion. This increase in circulating insulin level promotes glucose utilization by peripheral tissues and inhibits hepatic glucose output.

Non-insulin-dependent diabetes mellitus (NIDDM or Type II diabetes) is characterized by two pathological defects. One defect is insulin resistance of the major target tissues [Himsworth H. and Kerr R. B. (1942), Clin. Sci. 4:120; Kahn C. R. (1978), Metabolism. 27: 1893–1902; Olefsky J. M. (1981), Diabetes. 30:148–161; Reaven G. M. (1988), Diabetes. 37: 1595–1607; Kahn C. R. et al., in Pathogenesis of Non-Insulin Dependent Diabetes Mellitus. Grill V, Efendic S. Eds. (1988) New York Raven p. 227–239; DeFronzo R. A., et al (1992), Diabetes Care 15:318–368; Kolterman G et al. (1981), J. Clin. Invest. 68:957–969]. The other defect is the inability of the pancreas to fully compensate for this insulin resistance [Porte D. Jr. (1991), Diabetes. 40:166–180; Leahy J., et al. (1992), Diabetes Care 15:442–455; Turner R et al. (1992), Ann. Int. Med. 24:511–516]. During the early prediabetic years, insulin secretion is normal or increased. However, insulin secretion finally fails and is unable to compensate for insulin resistance, and it is this relative insulin deficiency that triggers hyperglycemia and clinically manifests Type II diabetes. Both genetic and environmental factors are postulated to be responsible for the progression from normal glucose tolerance to type II diabetes [Defronzo R A, et al (1992), Diabetes Care 15:318–368; Moller D E, Flier J S (1991), N. Engl. J. Med. 325:938–948. Taylor S. I. et al. (1991), J. Clin. Endocrinol. Metab. 73:1152–1163; Kahn C. R., (1994), Diabetes 43:1066–1084]. However, the exact mechanism of the insulin resistance of type II diabetes is still unclear.

Insulin resistance is generally defined as a reduced response to a given concentration of insulin. In Type II diabetes, this is manifested as a decreased ability of insulin to stimulate glucose uptake into muscle and fat, as well as to inhibit glucose production by the liver. In humans with obesity and Type II diabetes, there are multiple defects in insulin action including a decrease in insulin receptor and IRS-1 phosphorylation and a reduced PI 3-kinase activity [Defronzo R. A. et al (1992), Diabetes Care 15: 318–368; Kahn C. R. (1994), Diabetes 43:1066–1084; Kruszynska Y. T., Olefsky J. M. (1996), J. Invest Med. 44: 413–428]. In addition, impaired glucose transporter translocation and stimulation of glycogen synthesis have also been, shown [Rothman D. L. et al. (1992), J. Clin. Invest. 89: 1069–1075; Rothman D. L. et al. (1995), Proc. Natl. Acad. Sci. USA. 92: 983–987; Shulman, G. I. et al. (1990), N. Engl. J. Med. 322: 233–228; Ciaraldi T. P. et al. (1982), Diabetes 31:1016–1022]. Hyperinsulinemia and hyperglycemia, in addition to being secondary manifestations of insulin resistance, also have been shown to induce insulin resistance in target tissues. Insulin resistance in adipocytes is characterized by a decrease in both maximum insulin responsiveness as well as insulin sensitivity of the glucose transport system [Kashiwagi A. et al (1983), J. Clin. Invest. 72: 1246–1254; Marshall S., Olefsky J. M. (1980), J. Clin. Invest. 66: 763–772; Ciaraldi T. P. et al (1982), Diabetes 31: 1016–1022; Kolterman G. et al (1981), J. Clin. Invest. 68: 957–969]. Combined treatment of adipocytes with insulin and glucose causes a rapid and pronounced loss of both maxium insulin responsiveness and insulin sensitivity by impairing the response of translocation of glucose transporters to the cell surface [Garvey W T, et al (1987), J. Biol. Chem. 262: 189–197; Traxinger R R, Marshall S (1989), J. Biol. Chem. 264: 8156–8163].

The hexosamine biosynthesis pathway, in which fructose-6-phosphate is converted to glucosamine-6-phosphate, may be the pathway by which cells sense and respond to ambient glucose levels and, when glucose flux is excessive, down regulate glucose transport resulting in insulin resistant cells [Marshall, S., et al (1991), J. Biol Chem 266:4706–4712]. Glucose induced insulin resistance has been blocked by inhibiting glutamine:fructose-6-P amidotransferase (GFA), the rate-limiting enzyme of the hexosamine pathway [Marshall, S., et al (1991), J. Biol Chem 266:4706–4712]. Glucosamine, an agent known to preferentially enter the hexosamine pathway at a point distal to enzymatic amidation by GFA, bypasses the blockade and is 40-fold more potent than glucose in mediating insulin resistance [Marshall, S., et al (1991), J. Biol Chem 266:4706–4712; reviewed in Marshall S. et al (1991), FASEB J. 5: 3031–3036; McClain D. A., Crook E. D. (1996), Diabetes 45: 1003–1009]. Preexposure to glucosamine induces insulin resistance in skeletal muscle; the tissue responsible for the majority of insulin-dependent glucose utilization. Incubation of rat hemidiaphragm in 5–22 mmol/l glucosamine results in a 20–60% reduction in basal glucose transport and a significant reduction in the ability of insulin to increase glucose transport [Robinson, K. A. et al, (1993), Diabetes 42:1333–1346]. Glucosamine induces insulin resistance in vivo [Baron A. D. et al (1995), J. Clin. Invest. 96: 2792–2801; Rossetti L. et al (1995), J. Clin. Invest. 96:132–140].

A recently implicated important mediator of insulin resistance in obesity and diabetes is tumor necrosis factor-α (TNF-α), a cytokine produced primarily by activated macrophages [Beutler B. et al (1985), Nature 316: 552–554] and by adipocytes. TNF-α is overexpressed in adipose tissues in many animal models of obesity-Type II diabetes [Hotamisligil G. S., Spiegelman B. M. (1994), Diabetes 43: 1271–1278; Hotamisligil G. S., et al (1993), Science 259: 87–91; Skolnik E. Y., Marcusohn J. (1996), Cytokine & Growth Factor Reviews 7: 161–173] and is expressed in increased amounts from the fat of obese insulin-resistant humans [Hotamisligil G. S., et al (1995), J. Clin. Invest. 95: 2409–2415]. It has been shown to downregulate GLUT4 mRNA and protein levels in adipocytes [Hotamisligil G. S., et al (1993), Science 259: 87–91; Stephens J. M. et al (1997), J. Biol. Chem. 272: 971–976]. Administration of TNF-α to otherwise normal humans or animals results in a reduction in insulin sensitivity [R G. Douglas et al. (1991), Am. J. Physiol. 261, 606–612; T. Van Der Poll et al., ibid., p E457; C. H. Lang et al, Endocrinology 130, 43–52 (1992)]. Neutralization of TNF-α in obese insulin resistant rats improves insulin receptor signaling and insulin sensitivity of peripheral tissues [Hotamigsil G. S. et al (1993), Science 259: 87–91; Hotamisligil G. S. et al (1994), J. Clin. Invest. 1543–1549]. TNF-α treatment of cultured 3T3-L1 adipocytes provides a moderate reduction (20–50%) of insulin-stimulated insulin receptor autophosphorylation and a more pronounced effect on IRS-1 phosphorylation [Hotamisligil G. S. et al (1994), Proc. Natl. Acad. Sci. USA 91: 4854–4858; Feinstein R. et al (1993), J. Biol. Chem. 268: 26055–26058]. It has also been suggested that TNF-α induces insulin resistance via increased serine and threonine phosphorylation of IRS-1 [Hotarnisligil G. S. et al (1996), Science 271: 665–668; Kanety H. et al (1995), J. Biol. Chem. 270: 23780–23784].

Although significant progress has been made in defining the molecular mechanisms of different insulin resistance models, the primary biochemical signaling defects which induce insulin resistance in humans are not known.

Recent data suggest that there may be an association between insulin resistance and oxidative stress. Hyperglycemia and hyperinsulinemia may induce oxidative stress by increased generation of free radicals and reactive oxygen species (ROS) and/or impaired antioxidant defense systems [Wolff S. P., Dean R. T. (1987), Biochem J. 245: 243–250; Kashiwagi A. et al (1994), Diabetologia 37: 264–269; Wohaieb S. A., Godin D. V. (1987), Diabetes 36: 1014–1018]. Hyperglycemia-induced insulin resistance has also been reported to involve at least in part activation of protein kinase C (PKC) [Muller H. K. et al (1991), Diabetes 40: 1440–1448; Berti L. et al (1994), J. Biol. Chem. 269: 3381–3386; Takayama S, et al (1988), J. Biol. Chem 263: 3440–3447]. Further, hyperglycemia induced PKC activation in vascular cells has recently been shown to be prevented by vitamin E [Kunisaki M. et al (1994), Diabetes 43: 1372–1377]. In TNF-α signaling, increased ROS generation and oxidative stress may play a role. TNF-α has been shown to stimulate $H_2O_2$ production in fibroblasts and chondrocytes [Lo Y. Y. C. et al (1996), J. Biol. Chem. 271: 15703–15707; Sulciner D. J. et al (1996), Mol. Cell Biol. 16: 7115–7121]. ROS have been shown to function as second messengers in TNF-α induced c-fos expression and antioxidant treatment inhibited the induction of c-fos expression by TNF-α [Lo Y. Y. C. et al (1995), J. Biol. Chem. 270: 11727–11730; Meier B. et al (1989), Biochem J. 263: 539–545]. Thus, increased oxidative stress and ROS generation may be involved in TNF-α induced insulin resistance. Oxidative stress may be a common defect in diabetes that links metabolic and obesity-related insulin resistance together.

The current treatment of Type II diabetes includes dietary control, exercise, and stimulation of insulin secretion by oral sulphonylureas. As oral drug therapy aimed at controlling hyperglycemia in NIDDM often fails, insulin therapy is necessary in the late phase of type II diabetes. However, all these approaches do not completely overcome the major defect in type II diabetes: insulin resistance. Therefore, compounds that can correct insulin resistance may be useful in the treatment of NIDDM.

SUMMARY OF THE INVENTION

Chronic exposure of rat adipocytes in culture to high glucose and high insulin (high glucose/insulin) results in insulin resistance characterized by both a decreased maximum response and a decrease in sensitivity. The present inventor has significantly found that N-acetyl cysteine (NAC) at selected concentrations prevents or reverses the insulin resistance induced by high insulin/high glucose exposure, and in particular insulin resistance induced by glucosamine. N-acetyl cysteine may act by blocking TNF-α induced insulin resistance.

Therefore, broadly stated the present invention relates to a method of increasing insulin sensitivity or reducing insulin resistance in a subject comprising administering an effective amount of N-acetyl cysteine. N-acetyl cysteine provides an increase in insulin sensitivity or reduced insulin resistance i.e. an increase in response to a given concentration of insulin. The increase in insulin sensitivity/reduction in insulin resistance may be manifested as an increased ability of insulin to stimulate glucose uptake into muscle and fat, an inhibition of glucose production by the liver, an increase in insulin receptor and IRS-1 phosphorylation, increased PI 3-kinase activity, improved glucose transporter translocation, and/or stimulation of glycogen synthesis.

A method is also provided for preventing or treating a condition requiring increasing insulin sensitivity or reducing insulin resistance in a subject comprising administering to the subject an effective amount of N-acetyl cysteine.

The invention further provides a pharmaceutical composition for use in preventing or treating a condition requiring increasing insulin sensitivity comprising an effective amount of N-acetyl cysteine, and a pharmaceutically acceptable carrier, diluent, or excipient. The pharmaceutical compositions of the invention contain one or more active ingredient, as described herein, either alone or together with other active substances. Such pharmaceutical compositions can be for oral, topical, rectal, parenteral, local, inhalant or intracerebral use. They are therefore in solid or semisolid form, for example pills, tablets, creams, gelatin capsules, capsules, suppositories, soft gelatin capsules, gels, membranes, tubelets. For parenteral uses, those forms for intramuscular or subcutaneous administration can be used, or forms for infusion or intravenous or intracerebral injection can be used, and can therefore be prepared as solutions of the active substances or as powders of the active substances to be mixed with one or more pharmaceutically acceptable excipients or diluents, suitable for the aforesaid uses and with an osmolarity which is compatible with the physiological fluids. For local use, those preparations in the form of creams or ointments for topical use or in the form of sprays should be considered; for inhalant uses, preparations in the form of sprays, for example nose sprays, should be considered.

The preparations of the invention can be intended for administration to humans or animals. The dosage administered will vary depending on the use and known factors such as the pharmacodynamic characteristics of the particular substance, and its mode and route of administration; age, health, and weight of the individual recipient; nature and extent of symptoms, kind of concurrent treatment, frequency of treatment, and the effect desired. For example, an oral dose of between 100 mg–10 g, preferably 400 mg to 4 g, most preferably, 400 to 1600 mg of NAC daily (oral) is administered to a subject to prevent or treat conditions requiring increased insulin sensitivity or reduced insulin resistance in the subject.

The pharmaceutical compositions can be prepared by per se known methods for the preparation of pharmaceutically acceptable compositions which can be administered to patients, and such that an effective quantity of the active substance is combined in a mixture with a pharmaceutically acceptable vehicle. Suitable vehicles are described, for example, in Remington's Pharmaceutical Sciences (Remington's Pharmaceutical Sciences, Mack Publishing Company, Easton, Pa., USA 1985). On this basis, the pharmaceutical compositions include, albeit not exclusively, solutions of NAC in association with one or more pharmaceutically acceptable vehicles or diluents, and contained in buffered solutions with a suitable pH and iso-osmotic with the physiological fluids.

The active substance (i.e. NAC) or pharmaceutical compositions of the invention can be administered either alone or in conjunction with other therapeutic agents or other forms of therapy. The active substance or pharmaceutical composition can be used in combination with, for example, a suitable, biologically active form of chromium, vanadium, magnesium, manganese, lithium, zinc, potassium, or other minerals capable of exerting an influence upon carbohydrate metabolism; with vitamins C, E, or lipoic acid, carotenoids, CoEnzyme Q10, glutathione and its esters, other forms of cysteine or other biological antioxidants; with concentrates, extracts, or phytochemicals derived from plants e.g. cinnamon, camellia species, momordica species, gymnema species, gymnemic acid, catechin or other plant-sourced materials capable of exerting an influence upon carbohydrate metabolism; or fructose and any of its congeners/parent compounds capable of altering hepatic glucose metabolism, or a pharmaceutical composition of the invention can comprise such other agents. The active substance of the invention may be administered concurrently, separately, or sequentially with other therapeutic agents or therapies.

The pharmaceutical compositions and methods of the invention may be used to treat conditions requiring increasing insulin sensitivity or which are associated with insulin resistance however caused (including by free fatty acids and tumor necrosis factor-$\alpha$), and/or to prevent such conditions. Examples of such conditions include Type II diabetes, glucocorticoid induced insulin resistance, and obesity.

Other objects, features and advantages of the present invention will become apparent from the following detailed description. It should be understood, however, that the detailed description and the specific examples while indicating preferred embodiments of the invention are given by way of illustration only, since various changes and modifications within the spirit and scope of the invention will become apparent to those skilled in the art from this detailed description.

BRIEF DESCRIPTION OF THE DRAWINGS

The invention will now be described in relation to the drawings in which.

DESCRIPTION OF PREFERRED EMBODIMENTS OF THE INVENTION

The following examples are illustrative of the present invention:

The following materials and methods were used in the experiments described in the examples:

Materials:

Male Sprague-Dawley rats were from Charles-Rivers (Montreal, Que.). Dulbecco's Modified Eagle's Medium (DMEM), penicillin and streptomycin and fetal bovine serum were from GIBCO (Grand Island, N.Y.). Type I collagenase was from Worthington Biochemicals Corp. (Freehold, N.J.). Human insulin was from Eli Lilly Canada (Toronto, ON). 2-deoxy-D-[$^3$H]glucose (10 cl/mmol) was from Du Pont-New England Nuclear (Mississauga, ON). Nitex nylon was from Thompson (Scarborough, ON). Bovine serum albumin (fraction V) and all other chemicals were from Sigma (St. Louis, Mo.).

Preparation of Isolated Adipocytes:

Male Sprague-Dawley rats weighing 200–250 g were killed by cervical dislocation and epidydymal fat pads collected in 50 ml centrifuge tubes containing 20 ml 3% BSA-DMEM. Isolated adipocytes were obtained using a method modified from Rodbell (Rodbell, M. (1964) J. Biol. Chem. 239, 375–380). In brief adipose tissue was incubated in 3% BSA-DMEM containing 2 mg/ml collagenase for 1 hour at 37° C. Cells were then filtered through Nitex nylon (1000 $\mu$m), centrifuged at 500 rpm for 30 seconds and washed twice with 3% and 1% BSA-DMEM to remove collagenase. For resistant cells pretreated with NAC, cells were either incubated with 30 mM NAC for 2 hours at 37° C. before overnight incubation or co-incubated at 5 mM with the high insulin/high glucose or glucosamine.

Primary Culture and Washing Procedure: Freshly isolated adipocytes were incubated in 1% BSA-DMEM (pH 7.4) in 250 ml conical culture flasks at 37° C. with cells floating on top of the medium in a thin layer. Cells were incubated for 18 hours in a humidified atmosphere of 5% $CO_2$ and air. For control cells, the medium contained no insulin and 5.6 mM D-glucose. To induce insulin resistance, 600 ng/ml ($10^{-7}$ M) insulin and 20 mM D-glucose, or in the case of glucosamine 2.5 mM, were present in the medium. After overnight incubation, cells were washed two times in 3%BSA-KR30H, pH 7.0 (137 mM NaCl, 5 mM KCl, 1.2 mM $KH_2PO_4$, 1.2 mM $MgSO_4$, 1.25 mM $CaCl_2$, 30 mM HEPES, 1 mM sodium pyruvate and 3% BSA), and then further incubated in the same buffer for an additional 45 min to remove any remaining receptor bound insulin. Cells were then resuspended in 3% BSA-KRBH, pH 7.4 (118 mM NaCl, 5 mM KCl, 1.2 mM $MgSO_4$, 2.5 mM $CaCl_2$, 1.2 mM $KH_2PO_4$, 5 nM $NaHCO_3$, 30 mM HEPES, 1 mM sodium pyruvate and 3% BSA) and washed twice in the same buffer before 2-deoxyglucose uptake assay.

2-Deoxyglucose Transport Assay:

The method used was that described by Olefsky [Olefsky, J M. (1978), Biochem. J. 172, 137–145]5.0–6.0×$10^5$ cells/ml were used in the assay. Cells were preincubated at 37° C. for 30 min with a full range of insulin concentrations from 0 to 10 nM for 30 min. Initial rates of glucose uptake were measured by adding 100 $\mu$l of KRBH containing 1 $\mu$Ci of 2-Deoxy-D-[$^3$H] glucose and 2-deoxyglucose (final substrate concentration is 0.1 mM). At the end of 3 min, the reaction was terminated by adding ice cold 0.25 mM phloretin and separating cells (200 $\mu$l aliquot) from buffer by centrifugation through silicone oil as previously described [Marshall, S., Olefsky J M. (1980) J. Clin. Invest. 66:763–772]. To correct the 2-deoxyglucose uptake values for uptake of hexose by simple diffusion and non-specific trapping of radioactivity in the cells, glucose uptake was assessed in the presence of 0.25 mM phloretin. Nonspecific uptake (in the presence of phloretin) was subtracted from total uptake to yield specific uptake. In each experiment, glucose uptake was derived from the mean of duplicate determinations.

In Vivo Induction of Insulin Resistance and Assessment of Insulin Sensitivity in Rats:

Sprague-Dawley rats weighing 350–400 g were anesthetized and catheters were placed into the right internal jugular and left carotid arteries. The rats were allowed to recover for 5–7 days. Infusions of saline (control), or glucosamine (30 mmol/kg/min), with and without NAC (150 mg/kg over 1 hour, followed by 20 mg/kg/h) were carried out in awake, nonstressed rats for 7 hours. Two euglycemic clamps were performed consisting of an insulin infusion of 108 pmol/kg/min and adjusting the infusion rate of a 25% glucose solution to maintain normal glucose concentrations. The first clamp was carried out between 0–2 hours and the second between 5–7 hours, i.e. at the beginning and the end of the 7h infusion period. These procedures have been previously described [Miles, PDG, et al, (1988), Diabetes 47:395–400; and Rossetti, C. et al (1995), J. Clin. Invest. 96:132–140]. The infusion rate of glucose at steady state, that is, the final 30 min of the 2 hour clamp period, represents the glucose disposal rate and insulin sensitivity of peripheral tissues (mainly skeletal muscle) since at these insulin infusion rates hepatic glucose production is completely suppressed.

EXAMPLE 1

To test whether oxidative stress may play a role in the induction of insulin resistance, the effect of NAC, an antioxidant was tested. Preincubation of adipocytes with 30 mM NAC for 2 hours prior to the 18h exposure to high glucose plus insulin prevented in part the appearance of insulin resistance. Sensitivity of 2DG uptake to insulin was the same as in control cells while responsiveness expressed relative to basal 2 DG uptake was even higher. However in NAC pretreatment of the insulin resistant adipocytes there was only slight improvement in absolute rates of insulin-stimulated 2DG uptake. The increase in responsiveness was secondary to a significant lowering of basal uptake by NAC. It should be noted that NAC decreased both basal and insulin-stimulated glucose uptake in control adipocytes. Thus, although the decrease in insulin sensitivity was clearly prevented by NAC pretreatment, the improvement in insulin responsiveness is less obvious (data not shown).

EXAMPLE 2

Co-Incubation of NAC with High Insulin-High Glucose

Figure 1:
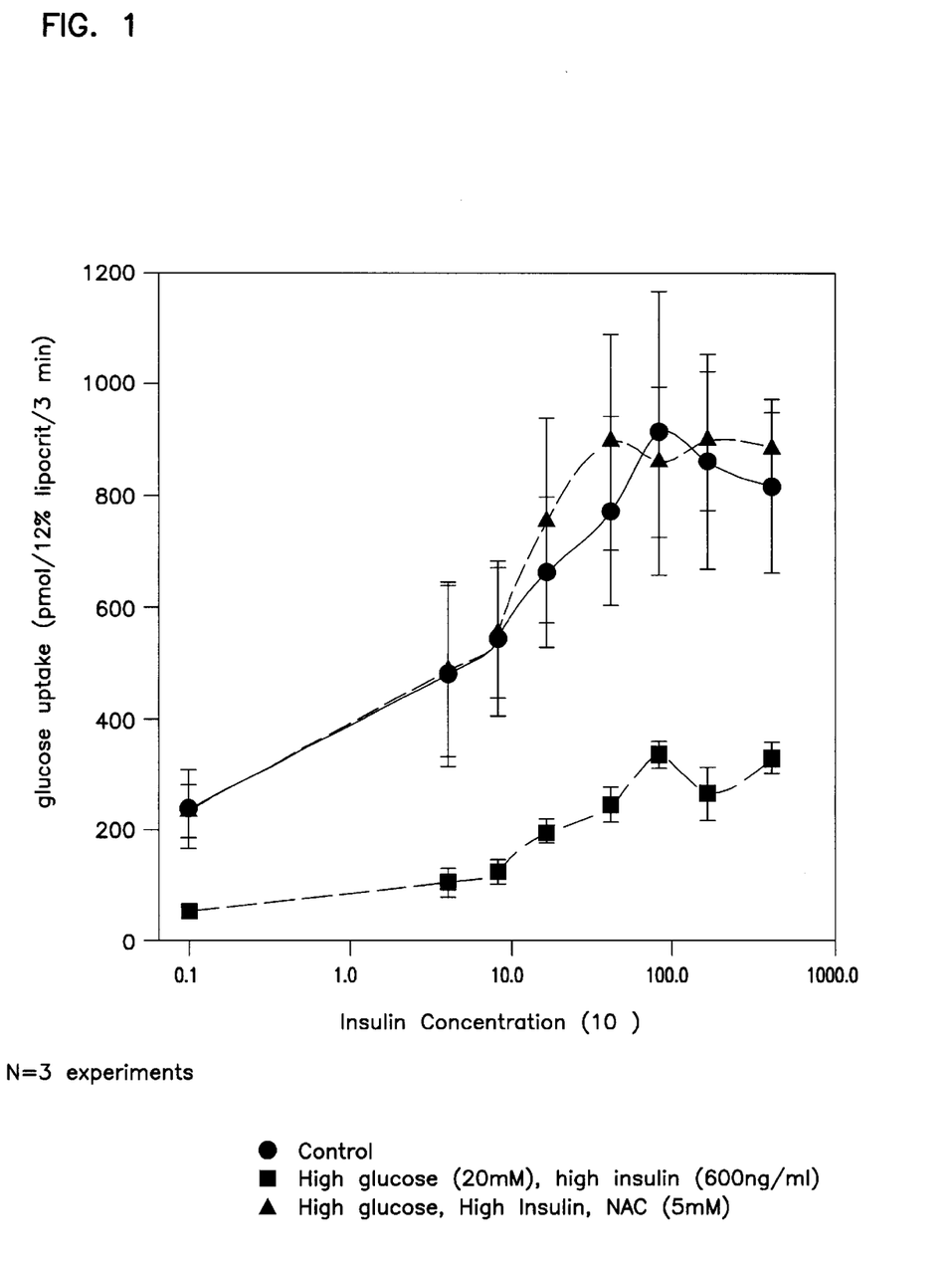
FIG. 1 is a graph showing the effect of NAC to reverse/prevent the high insulin and high glucose induced insulin resistance.
Figure 2:
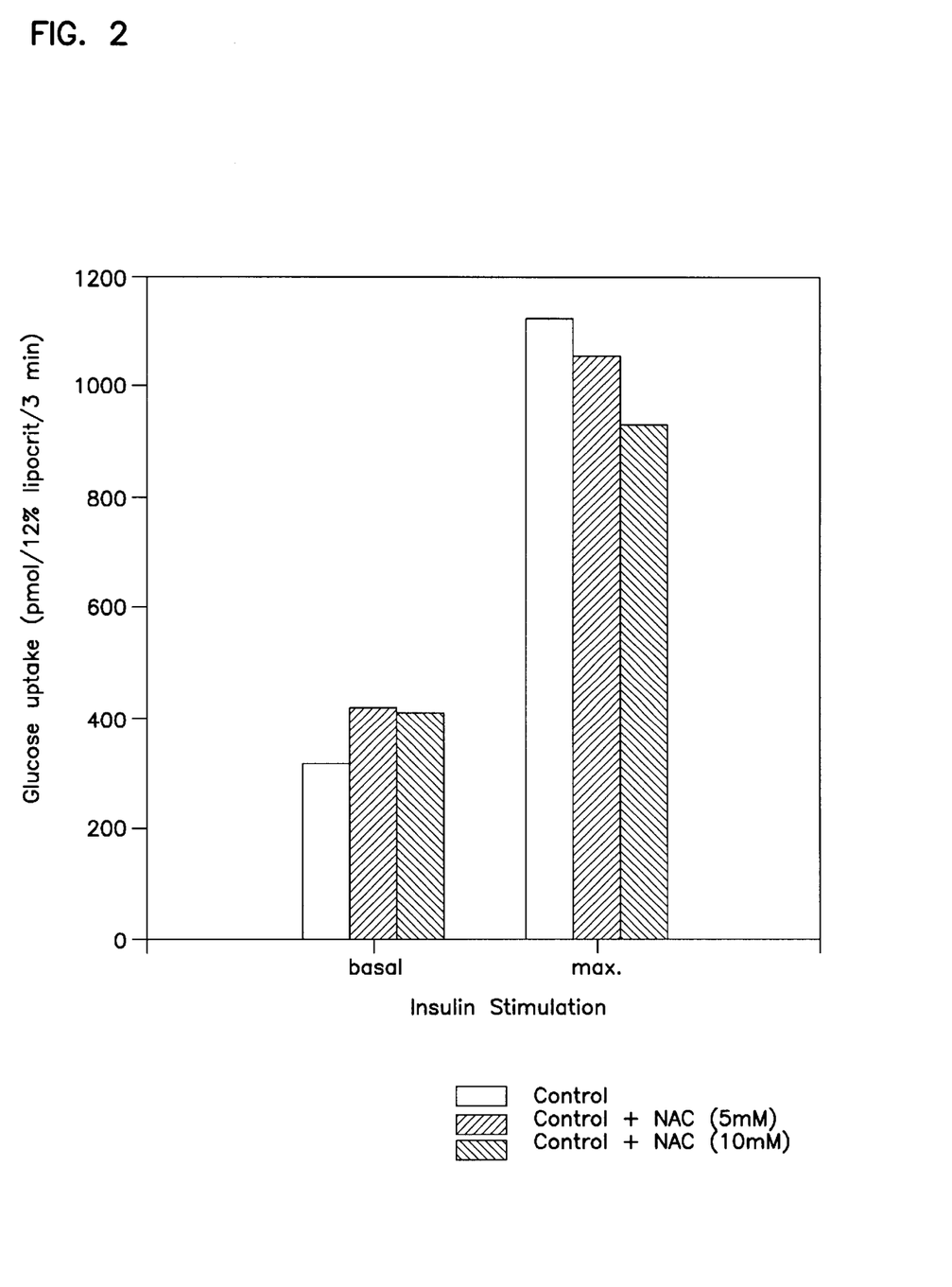
FIG. 2 is a graph showing the lack of effect of NAC on control cells.

The previous results showed that pre-treatment of adipocytes with a high concentration of NAC (30 mM) prevented the decrease in insulin sensitivity caused by the high insulin/high glucose exposure but NAC itself caused a decrease in maximum insulin response. Therefore, a second protocol was developed to maintain the NAC treatment at a lower concentration in the presence of the high insulin/high glucose. NAC at 5 mM maintained throughout the incubation was able to prevent/reverse the insulin resistance induced by the high insulin/high glucose exposure (FIG. 1). In contrast to the pre-treatment protocol described above, both the sensitivity and maximum response to insulin was normalized. Unlike 30 mM, NAC alone at 5 mM did not impair basal or insulin-stimulated uptake in control adipocytes (FIG. 2).

EXAMPLE 3

Figure 3:
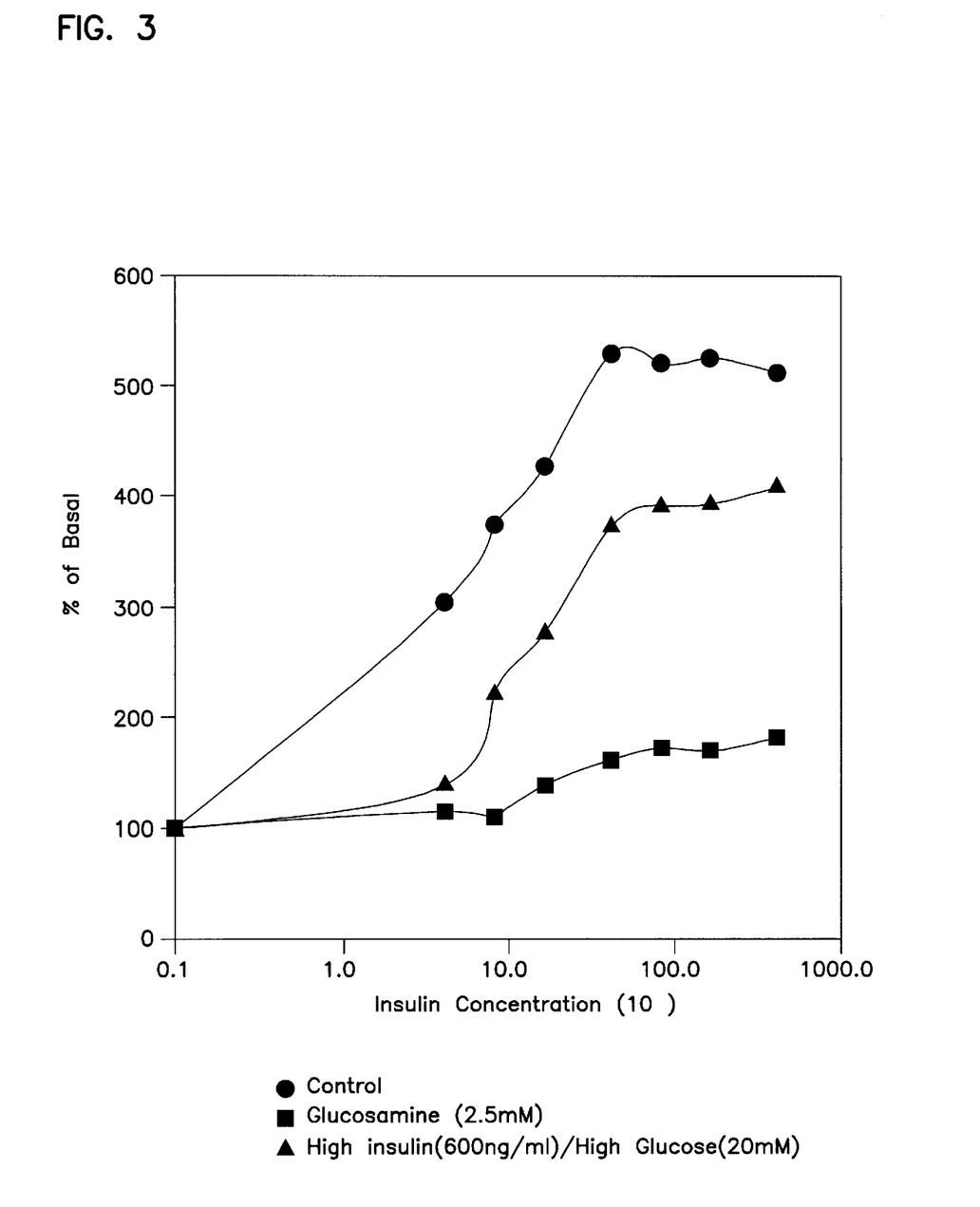
FIG. 3 is a graph showing that glucosamine also causes insulin resistance (%Basal)
Figure 4:
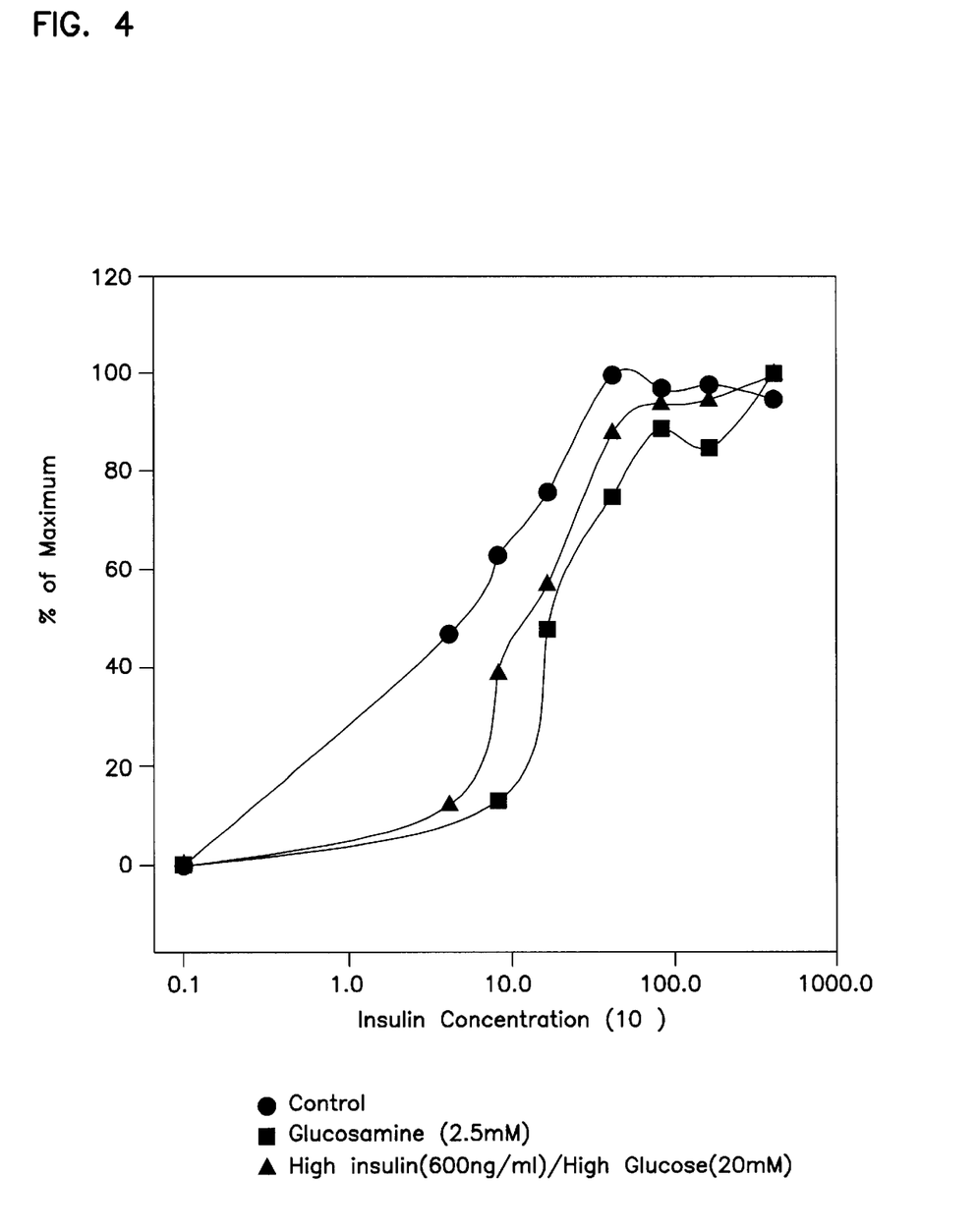
FIG. 4 is a graph of the data in FIG. 3 expressed as % maximum.

High Insulin/High Glucose Exposure Induces Insulin Resistance via the Hexosamine Synthesis (Glucosamine) Pathway Previous studies have demonstrated that the high insulin/high glucose combination acts to cause insulin resistance by promoting glucose flux through the hexosamine biosynthesis pathway which requires the enzyme glutamine fructose-phosphate aminotransferase (GFA). One product of this pathway is glucosamine and one can mimic the insulin resistance by exposing adipocytes directly to glucosamine. This bypasses the requirement for GFA. Experiments demonstrated that glucosamine, 2.5 mM can induce insulin resistance similar to that caused by the high insulin/high glucose protocol. Thus, both a shift to the right (decreased sensitivity) in the insulin dose response curve and a decrease in maximum response is observed (FIG. 3 and FIG. 4).

EXAMPLE 4

NAC Reverses the Insulin Resistance Caused by Glucosamine

Figure 5:
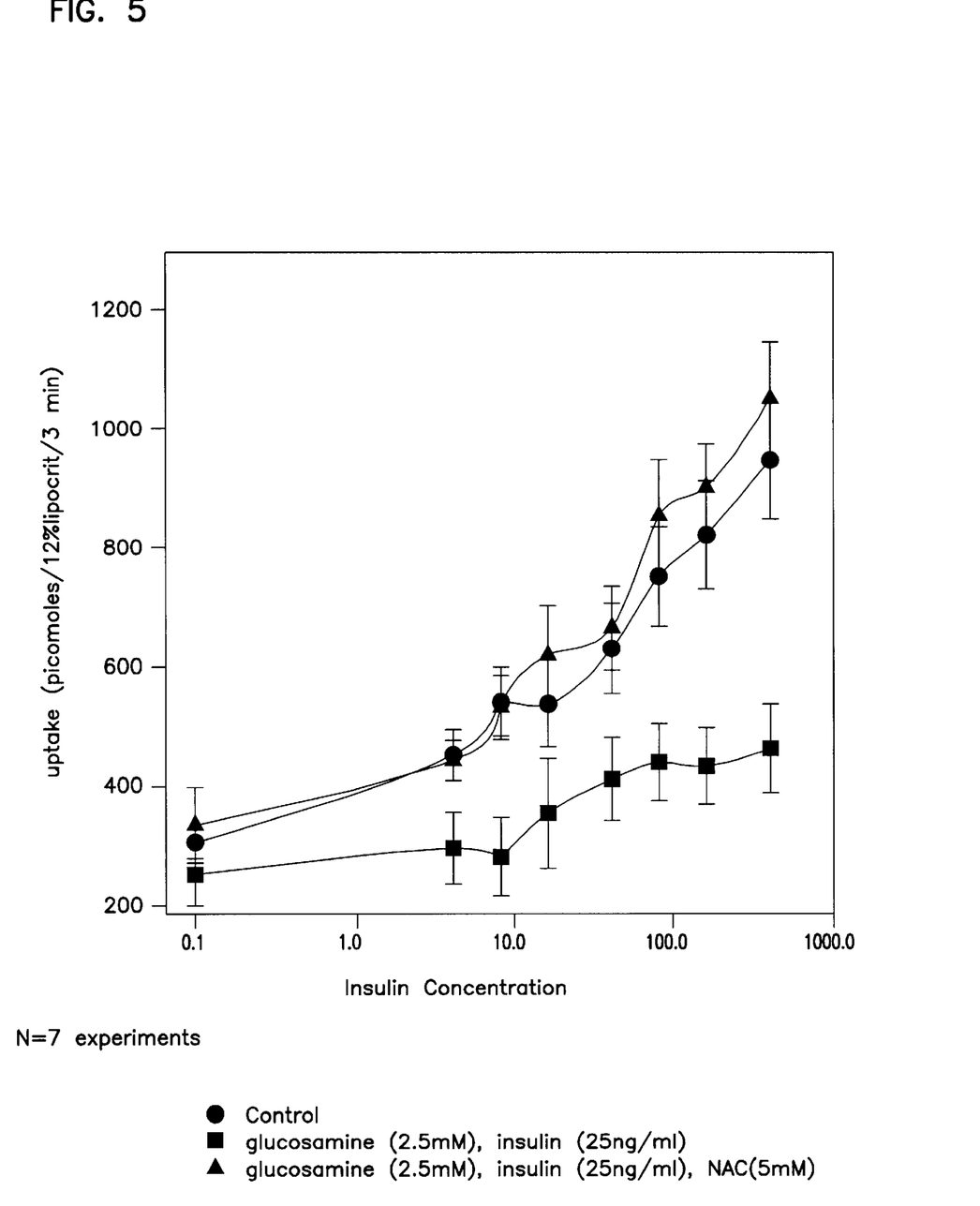
FIG. 5 is a graph showing the effect of NAC to prevent/reverse the glucosamine induced insulin resistance.

To test the site of action of the antioxidant NAC, to improve insulin resistance, i.e. prior to or at the enzyme GFA, or distal to the formation of glucosamine, adipocytes were co-incubated with glucosamine 2.5 mM and NAC 5 mM. Under these conditions NAC was able to prevent/reverse the insulin resistance (FIG. 5).

EXAMPLE 5

Figure 6:
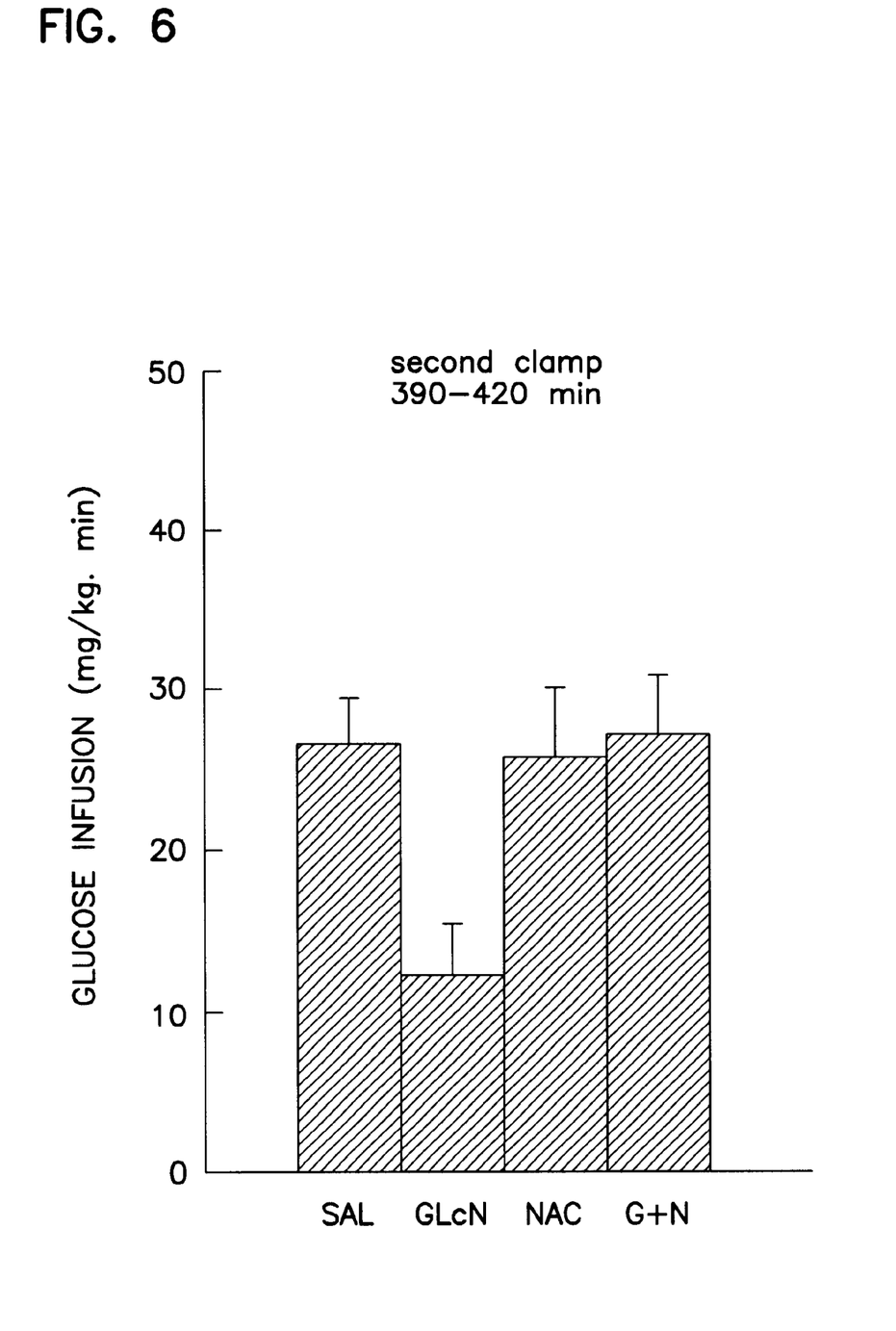
FIG. 6 is a graph showing that NAC was able to prevent insulin resistance induced by glucosamine in the intact rat.

To test whether NAC was effective in the intact animal, rats were rendered insulin resistant by intravenous infusion of glucosamine over 7 hours. This has previously been demonstrated to result in insulin resistance of peripheral target tissues, fat and muscle, as measured by the glucose disposal rate into these tissues in response to an infusion of insulin at steady state. This model of insulin resistance was established and a co-infusion of NAC was tested. NAC was able to prevent the insulin resistance induced by glucosamine in the intact rat (FIG. 6). The glucose disposal rate remained in the normal range. NAC did not significantly alter glucose disposal rate in control rats (saline-infused). Furthermore, steady state levels of glucose were the same during the different infusion protocols.

EXAMPLE 6

Chronic exposure to high glucose concentrations combined with insulin (high G/I) causes insulin resistance (IR) and has been associated with oxidative stress but the role of oxidative stress in the pathogenesis of IR remains unclear. The ability of various antioxidants to prevent insulin resistance in freshly isolated rat adipocytes (adip) exposed to 20 mM G plus $10^{-7}$ M I was examined. While coincubation with 250 1 M a-tocopherol (Vit E) or ascorbic acid (Vit C) had no significant effect, 5 mM NAC completely inhibited the decrease in basal and 1-stimulated 2-deoxyglucose (2DG) uptake (pmol/6×$10^5$ cells/3 min: Basal-control 240"71, Resist 55"11, Resist+NAC 235"47; Maximum I—control 816"155; Resist 326"27; Resist+NAC 885"63; p<0.01, Resist vs others). NAC alone did not alter 2DG uptake. Coincubation with GSH ester (cell permeable reduced glutathione) also prevented IR.

Fractionation of adip lysates and immunoblotting revealed that high G/I reduced I-stimulated GLUT 4 translocation from LDM (low density microsomes) to PM (plasma membranes) by 50% and LDM-associated (ser 473 phosphorylated akt/PKB) by 40%. Total akt/PKB was unchanged. NAC prevented the defects in GLUT 4 translocation and akt/PKB phosphorylation. To determine whether NAC was effective in vivo rats were infused with saline or G to achieve steady state G concentrations of 15 mM for 6 h with and without NAC. Euglycemic hyperinsulinemic clamps at 6–8 h revealed that hyperglycemia caused IR which was prevented by coinfusion of NAC (glucose uptake, mg/kg/min: control 43.8" 1.1; Resist 30.5" 1.5; Rest+NAC 45.6" 0.3; p<0.01, Resist vs others). NAC alone had no effect. High G/I—mediated IR is prevented by NAC and GSH ester, but not by Vit E or Vit C. The data indicate a specific role for GSH in the pathogenesis of IR and NAC as a novel therapeutic agent.

EXAMPLE 7

NAC (N-acetylcysteine) Prevents Hyperglycemia and Glucosamine-induced Insulin Resistance in vitro and in vivo by Different Mechanisms Insulin resistance (IR) is prevented by NAC in isolated rat adipocytes (adip) cultured in high glucose plus insulin (high G/I) and in rats infused with glucose. The mechanism of high G/I mediated IR has been suggested to involve enhanced flux through the hexosamine biosynthesis pathway (HBP) via glutamine fructose amidotransferase and increased synthesis of UDP-N acetylhexosamines (UDP-HexNAc) as IR is induced by glucosamine. To investigate the site of NAC action adip were rendered insulin resistant by exposure to 5.0 mM glucosamine and rats were infused with glucosamine for 7 h with a euglycernic hyperinsulinemic clamp performed during the first and final 2 h. Coincubation of adip with NAC and coinffusion of NAC with glucosamine completely prevented IR in vitro and in vivo. NAC alone had no effect.

To examine the potential role of the HBP, total UDP-Hxn NAc (UDP-Glc NAc plus UDP-Gal NAc) was determined by HPLC. High G/I modestly, while glucosarnine markedly increased UDP-Hex NAc (pmol/ml cells-control 6.7±0.47, high G/I 10.2±0.52, glucosamine 38.4±0.90, p<0.01 for both vs control). Coincubation with NAC normalized the increased UDP-Hex NAc by high G/I (7.2±0.41) but not that by glucosamine (25.7±3.27). ATP depletion has been suggested to be the cause of IR induced by glucosamine. Total cellular ATP was significantly reduced (40%) in adip exposed to glucosamine and this decrease was inhibited by NAC. High G/I treatment did not alter ATP.

In conclusion: 1) NAC prevents both high G/I and glucosamine-induced IR in vitro and in vivo 2) reversal of ATP depletion but not the elevated UDP-HexNAc associated with glucosamine prevents IR, while 3) NAC prevents IR and the associated increase in UDP-HexNAc induced by high G/I. NAC is indicated as a novel therapy for IR.

While the present invention has been described with reference to what are presently considered to be the preferred examples, it is to be understood that the invention is not limited to the disclosed examples. To the contrary, the invention is intended to cover various modifications and equivalent arrangements included within the spirit and scope of the appended claims.

All publications, patents and patent applications are herein incorporated by reference in their entirety to the same extent as if each individual publication, patent or patent application was specifically and individually indicated to be incorporated by reference in its entirety.

I claim:

1. A method of increasing insulin sensitivity or reducing insulin resistance a subject comprising administering an effective amount of N-acetyl cysteine.

2. A method as claimed in claim 1 wherein the insulin resistance is induced by glucosamine.

3. A method as claimed in claim 1 wherein the concentration of N-acetyl cysteine is 100 mg to 10 g daily.

4. A method for preventing or treating a condition requiring increasing insulin sensitivity or reducing insulin resistance in a subject comprising administering to the subject an effective amount of N-acetyl cysteine.

* * * * *